(12) United States Patent
Brekkan et al.

(10) Patent No.: US 9,409,967 B2
(45) Date of Patent: Aug. 9, 2016

(54) METHOD FOR PURIFICATION OF CLEAVED PRO-INSULIN

(71) Applicant: GE HEALTHCARE BIO-SCIENCES AB, Uppsala (SE)

(72) Inventors: Eggert Brekkan, Uppsala (SE); Kjell Eriksson, Uppsala (SE); Bo-Lennart Johansson, Uppsala (SE); Jamil Shanagar, Uppsala (SE)

(73) Assignee: GE Healthcare BioProcess R&D AB, Uppsala (SE)

( * ) Notice: Subject to any disclaimer, the term of this patent is extended or adjusted under 35 U.S.C. 154(b) by 7 days.

(21) Appl. No.: 14/348,634

(22) PCT Filed: Sep. 28, 2012

(86) PCT No.: PCT/SE2012/051040
§ 371 (c)(1),
(2) Date: Mar. 31, 2014

(87) PCT Pub. No.: WO2013/048330
PCT Pub. Date: Apr. 4, 2013

(65) Prior Publication Data
US 2014/0243498 A1     Aug. 28, 2014

(30) Foreign Application Priority Data
Sep. 30, 2011    (SE) ...................................... 1100722

(51) Int. Cl.
| | | |
|---|---|---|
| C07K 1/18 | (2006.01) | |
| A61K 38/28 | (2006.01) | |
| B01D 15/08 | (2006.01) | |
| B01D 15/26 | (2006.01) | |
| B01D 15/36 | (2006.01) | |
| B01J 20/285 | (2006.01) | |
| B01J 20/286 | (2006.01) | |
| B01J 20/32 | (2006.01) | |
| C07K 14/62 | (2006.01) | |
| B01J 39/26 | (2006.01) | |
| B01J 20/288 | (2006.01) | |

(52) U.S. Cl.
CPC .............. *C07K 14/62* (2013.01); *B01D 15/362* (2013.01); *B01J 20/286* (2013.01); *B01J 20/288* (2013.01); *B01J 20/321* (2013.01); *B01J 20/3212* (2013.01); *B01J 20/3293* (2013.01); *B01J 39/26* (2013.01); *B01D 15/361* (2013.01)

(58) Field of Classification Search
None
See application file for complete search history.

(56) References Cited

U.S. PATENT DOCUMENTS

| | | |
|---|---|---|
| 4,129,560 A | 12/1978 | Zoltobrocki |
| 5,101,013 A | 3/1992 | Dorschug et al. |
| 5,977,297 A | 11/1999 | Obermeier et al. |
| 6,426,315 B1 | 7/2002 | Bergstrom et al. |
| 6,710,167 B1 | 3/2004 | Sievers et al. |
| 2011/0155668 A1 | 6/2011 | Glad et al. |

FOREIGN PATENT DOCUMENTS

| | | |
|---|---|---|
| DE | 3511270 | 10/1986 |
| EP | 0013826 | 8/1980 |
| GB | 1 054 523 | 10/1965 |
| GB | 1 285 024 | 8/1972 |
| GB | 2 173 503 | 10/1986 |
| WO | WO 2011/102790 | 8/2011 |

OTHER PUBLICATIONS

Data file 28-9837-63 AC, "Ion exchange chromatography: Capto™ SP ImpRes, Capto Q ImpRes" GE Healthcare Life Sciences, 28-9837-63 AC, pp. 1-12, first published Jan. 2011—see p. 12, right col. I. 9.*
Application note 29-0018-56 AB, "High-throughput process development and scale-up of an intermediate purification step for recombinant insulin," GE Healthcare Life Sciences, 29-0018-56 AB, pp. 1-8, first published Jun. 2012—see p. 8, right col. I. 11.*
Shanagar et al., "Development of capture and intermediate chromatography steps for insulin purification," available at URL: processdevelopmentforum.com/posters/development-of-capture-and-intermediate-chromatography-steps-for-insulin-purification/ (published online Aug. 25, 2011, pp. 1-13), accessed Dec. 20, 2014.*

* cited by examiner

*Primary Examiner* — Julie Ha
*Assistant Examiner* — Kristina M Hellman
(74) *Attorney, Agent, or Firm* — Wood IP LLC

(57) ABSTRACT

The present invention is within the field of biomolecule purification. More closely the invention relates to chromatographic purification of insulin using a specific kind of shell beads having an inner core and an outer functionalized layer. The method enables purification at high flow rates and high purity, over 90%.

14 Claims, 3 Drawing Sheets

METHOD FOR PURIFICATION OF CLEAVED PRO-INSULIN

CROSS-REFERENCE TO RELATED APPLICATIONS

This application is a filing under 35 U.S.C. 371 of international application number PCT/SE2012/051040, filed Sep. 28, 2012, published on Apr. 4, 2013 as WO 2013/048330, which claims priority to application number 1100722-6 filed in Sweden on Sep. 30, 2011.

FIELD OF THE INVENTION

The present invention is within the field of biomolecule purification. More closely the invention relates to chromatographic purification of insulin using a specific kind of shell beads having an inner core and an outer functionalized layer. The method enables purification in very high purity, over 90%.

BACKGROUND OF THE INVENTION

Insulin is produced either in bacteria (*E. coli*) or yeast. In the case of bacteria the insulin (expressed as pro-insulin) is produced in inclusion bodies which after denaturation, refolding and renaturation is purified by several steps. Normally several chromatography steps are combined with filtration steps, enzymatic cleavage of pro-insulin to insulin, precipitation crystallization and formulation steps. In the case of a yeast expression system no inclusion bodies are formed, besides this the process is quite similar to the bacterial one.

Insulin is produced at several tons a year and the use of insulin is increasing for every year. More and more people will get diabetes, not the least in the developing world. The increase in demand of insulin makes it necessary to utilize efficient production methods and processes. Yield is ever important and a method giving a higher yield normally gives a better process economy, translating to a more affordable product. The affordability is a key parameter in making the product available to a broader base of patients. This is also important so one does not put an unnecessary constraint on a healthcare sector that is suffering under an increase cost pressure.

Thus, it would be desirable to have a faster, more economic method for insulin production giving a pure product in high yield.

Chromatography purification of insulin using shell beads has not been suggested before.

SUMMARY OF THE INVENTION

The invention provides an insulin purification method in which the loading of the chromatography media (gram product loaded per ml chromatography media) can be increased threefold compared with conventional technique, reducing the consumption of chromatography media. This can directly be translated to a more cost effective process. In addition the method using shell beads in a chromatography step described herein, can be operated at a higher velocity making the process more economical by enabling more product to be produced in a given time, i.e. by shortening the time for this particular chromatography step.

The present invention provides a method for biomolecule purification using shell beads that are characterized by being functionalized only in the outermost layer of the bead, i.e., the functional ligand is only found in the outermost layer and not in the core of the bead. The thickness of the functionalized layer can be controlled and the core of the bead which is non-functionalized can either be filled with for example dextran or left empty.

A chromatographic bead with a functionalized layer has the potential of having a resolution comparable to that on a much smaller fully functionalized bead, while maintaining the better pressure-flow properties of the larger bead. The capacity of the shell bead will essentially be reflected by the fraction of the bead volume functionalized and will thus be lower than on a fully functionalized bead of the same size.

Thus, the present invention relates to a method for purification of insulin from pro-insulin comprising loading a sample of cleaved pro-insulin on a chromatography medium comprising porous shell beads having an inner core and an outer functionalized layer provided with ion exchange ligands; adsorbing insulin on the ligands; and eluting insulin from the chromatography medium at a flow rate of 100-1000 cm/h, preferably 300-600 cm/h, wherein the eluted insulin has a purity of more than 85%, preferably more than 90%.

The shell beads used in the method are 20-100 µm in diameter, preferably 40-80 µm in diameter.

The functionalized layer of the shell beads comprises a 3-9 µm thick layer, preferably a 5-7 µm thick layer.

The ion exchange ligand is a strong cation exchange group, such as sulphonate ($SO_3^-$), sulphate ($—OSO_3^-$), phosphate ($—OPO_3^{2-}$) and phosphonate ($PO_3^{2-}$).

In one embodiment the core of the shell beads is filled with a suitable polar polymer in order to make the core more dense which gives better resolution (narrow peaks). The polar polymer may be agarose, dextran, cellulose, starch, pullulan or a completely synthetic polymer such as polyacrylic amid, polymethacrylic amide, poly(hydroxyalkylacrylates).

DETAILED DESCRIPTION OF THE INVENTION

The invention will be described more closely below in association with some non-limiting examples.

Materials and Methods

Figure 1:
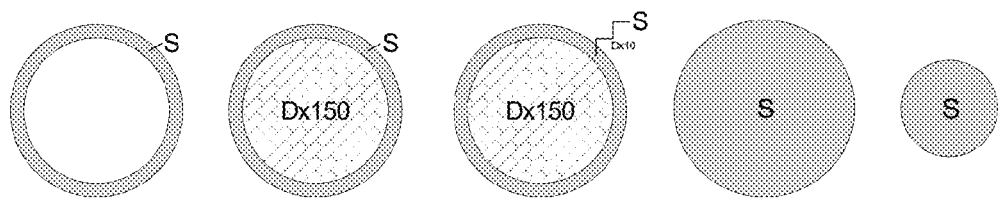
FIG. 1 Schematic view of shell beads used in the purification method of the present invention.

Presented herein are the results on three different shell bead constructs based on Sepharose HFA 55 and two reference prototypes/resins (FIG. 1, Table 1).

From left to right in FIG. 1: Prototype S6: S-ligand in outermost layer and core left unfunctionalized, Prototype S20: As prototype S6, but core filled with dextran T150 (Mp 150,000), Prototype S26: As prototype S20, but the S-ligand is coupled on a dextran extender (Mp 10,000), Prototype S12: reference prototype where the whole bead is functionalized, and Capto SP ImpRes. The first four prototypes have a particle size of 77 µm, while Capto SP ImpRes has a particle size of 40 µm.

TABLE 1

Properties of tested prototypes.

| Prototype | Particle diameter (μm) | Shell thickness (μm) | Ligand density (LD) (μmol/ml) | Function volume fraction | LD/functional volume μmol/ml |
|---|---|---|---|---|---|
| S6 | 77.5 | 6.41 | 42 | 0.42 | 163 |
| S12 ref | 77.5 | Full | 103 | 1 | 167 |
| S20 | 77.5 | 6.51 | 42 | 0.42 | 161 |
| S26 | 77.5 | 7.78 | 50 | 0.49 | 166 |

Preparation of Shell Media Based on Sepharose HFA 55

Synthesis of Prototype S6
Allyl Activation of Sepharose HFA 55

Sepharose HFA 55 was washed with distilled water on a glass filter. The gel, 700 mL drained gel, was weighed into a 3-necked round bottomed flask. NaOH (/700 mL, 50%-solution) was added and mechanical stirring was started. The slurry was heated to 50° C. on a water bath. After approximately one hour, 126 mL of allyl glycidyl ether (AGE) was added. The slurry was then left under vigorously stirring over night. After about 20 hours the slurry was transferred to a glass filter and washed with distilled water (×4), ethanol (×4) and distilled water (×4).

The allyl content was then determined by titration: 215 μmol/mL.
Shell Activation (Partial Bromination)

Allylated gel, 100 mL, was weighed into a flask and 100 mL of distilled water was added. 0.524 mL bromine was dissolved in 800 mL distilled water and was added to the allylated gel slurry. This amount of bromine is supposed to give (corresponds to) a shell thickness of about 7.5 μm. The bromine solution was momentary added to the allyl gel slurry during vigorous stirring. After approximately 10 minutes the gel was washed with distilled water on a glass filter.
Shell Coupling of the $SO_3^-$-Groups 100 mL of the partially brominated gel (see above) was transferred to a flask and mixed with 10 g of sodium sulphite dissolved in 100 mL distilled water. While stirring, 50% NaOH is added to pH 12, followed by stirring for 16 h at 50° C. and washings on a glass filter with distilled water. The gel was then washed with distilled water on a glass filter.

The amount of $SO_3^-$-groups attached was estimated to 43 μmol/mL.
Core Allyl Removal 50 mL of S-shell gel (see above) was mixed with 20% (v/v) thioglycerol dissolved in distilled water (50 mL). The pH was adjusted to 10 followed by stirring for 20 h at 50° C. The gel was then washed with distilled water on a glass filter.
Synthesis of Prototype S12
Allyl Activation of Sepharose HFA 55

Sepharose HFA 55 was washed with distilled water on a glass filter. The gel, 700 mL drained gel, was weighed into a 3-necked round bottomed flask. NaOH (/700 mL, 50%-solution) was added and mechanical stirring was started. The slurry was heated to 50° C. on a water bath. After approximately one hour, 245 mL of allyl glycidyl ether (AGE) was added. The slurry was then left under vigorously stirring over night. After about 20 hours the slurry was transferred to a glass filter and washed with distilled water (×4), ethanol (×4) and distilled water (×4).

The allyl content was then determined by titration: 290 μmol/mL.

Activation (Bromination) of the Beads

Allylated gel, 50 mL, was weighed into a flask and 50 mL of distilled water and 2.0 g sodium acetate were added. A Bromine (saturated aqueous solution) was added until a persistent yellow colour was obtained, followed by destruction of excess bromine with sodium-formiate and washings with distilled water on a glass filter.
Coupling of the $SO_3^-$-Groups 50 mL brominated gel (see above) was transferred to a flask and mixed with 10 g of sodium sulphite dissolved in 25 mL distilled water. While stirring, 50% NaOH is added to pH 12, followed by stirring for 18 h at 50° C. The gel was then washed with distilled water on a glass filter.

The amount of $SO_3^-$-groups attached was estimated to 103 μmol/mL.
Synthesis of Prototype S20
Allyl Activation of Sepharose HFA 55

Sepharose HFA 55 was washed with distilled water on a glass filter. The gel, 700 mL drained gel, was weighed into a 3-necked round bottomed flask. NaOH (/700 mL, 50%-solution) was added and mechanical stirring was started. The slurry was heated to 50° C. on a water bath. After approximately one hour, 126 mL of allyl glycidyl ether (AGE) was added. The slurry was then left under vigorously stirring over night. After about 20 hours the slurry was transferred to a glass filter and washed with distilled water (×4), ethanol (×4) and distilled water (×4).

The allyl content was then determined by titration: 215 μmol/mL.
Shell Activation (Partial Bromination)

Allylated gel, 100 mL, was weighed into a flask and 100 mL of distilled water was added. 0.524 mL bromine was dissolved in 800 mL distilled water and was added to the allylated gel slurry. This amount of bromine is supposed to give (corresponds to) a shell thickness of about 7.5 μm. The bromine solution was momentary added to the allyl gel slurry during vigorous stirring. After approximately 10 minutes the gel was washed with distilled water on a glass filter.
Shell Coupling of the $SO_3^-$-Groups 100 mL of the partially brominated gel (see above) was transferred to a flask and mixed with 10 g of sodium sulphite dissolved in 100 mL distilled water. While stirring, 50% NaOH is added to pH 12.5, followed by stirring for 18 h at 50° C. The gel was then washed with distilled water on a glass filter.

The amount of $SO_3^-$-groups attached was estimated to 43 μmol/mL.
Activation (Bromination) of the Core 50 mL of the shell coupled beads (see above) was weighed into a flask and 50 mL of distilled water and 2.0 g sodium acetate were added. A Bromine (saturated aqueous solution) was added until a persistent yellow colour was obtained, followed by destruction of excess bromine with sodium-formiate and washings with distilled water on a glass filter.
Dextran Coupling in the Core of the Beads 50 g of Dextran (MW: 150 000 g/mol) were dissolved in 50 mL of distilled water by slow stirring at ambient temperature for 2-4 h. 50 mL drained core activated HFA 55 beads ($SO_3^-$-groups attached in the shell) were added to the dextran solution, and the solution was stirred at 50° C. for 1 h. While stirring, 6.25 mL of 50% NaOH was added. The solution was stirred for 16 h at 50° C. and then washed on a glass filter with distilled water.
Synthesis of Prototype S26
Allyl Activation of Sepharose HFA 55

Sepharose HFA 55 was washed with distilled water on a glass filter. The gel, 400 mL drained gel, was weighed into a 3-necked round bottomed flask. NaOH (400 mL, 50%-solution) was added and mechanical stirring was started. The slurry was heated to 50° C. on a water bath. After approximately one hour, 72 mL of allyl glycidyl ether (AGE) was added. The slurry was then left under vigorously stirring over night. After about 20 hours the slurry was transferred to a glass filter and washed with distilled water (×4), ethanol (×4) and distilled water (×4).

The allyl content was then determined by titration: 215 µmol/mL.

Activation (Bromination) of the Beads 400 mL of the allylated beads (see above) was weighed into a flask and 500 mL of distilled water and 2.0 g sodium acetate were added. A Bromine (saturated aqueous solution) was added until a persistent yellow colour was obtained, followed by destruction of excess bromine with sodium-formiate and washings with distilled water on a glass filter.

Dextran Coupling 320 g of Dextran (MW: 10 000 g/mol) were dissolved in 400 mL of distilled water by slow stirring at ambient temperature for 2-4 h. 400 mL drained activated HFA 55 beads (see above) were added to the dextran solution, and the solution was stirred at 50° C. for 1 h. While stirring, 50 mL of 50% NaOH was added. The solution was stirred for 16 h at 50° C. and then washed on a glass filter with distilled water. The amount of dextran attached was 17 mg/mL.

Allyl Activation of Dextran Modified Sepharose HFA 55

Dextran modified Sepharose HFA 55 was washed with distilled water on a glass filter. The gel, 200 mL drained gel, was weighed into a 3-necked round bottomed flask. NaOH (200 mL, 50%-solution) was added and mechanical stirring was started. The slurry was heated to 50° C. on a water bath. After approximately one hour, 36 mL of allyl glycidyl ether (AGE) was added. The slurry was then left under vigorously stirring over night. After about 16 hours the slurry was transferred to a glass filter and washed with distilled water (×4), ethanol (×4) and distilled water (×4).

The allyl content was then determined by titration: 220 µmol/mL.

Shell Activation (Partial Bromination)

Allylated gel, 50 mL, was weighed into a flask and 500 mL of distilled water was added. 0.27 mL bromine was dissolved in 50 mL distilled water and was added to the allylated gel slurry. This amount of bromine is supposed to give (corresponds to) a shell thickness of about 7.5 µm. The bromine solution was momentary added to the allyl gel slurry during vigorous stirring. After approximately 10 minutes the gel was washed with distilled water on a glass filter. The rest allyl content (allyl groups in the core of the beads) was 130 µmol/mL.

Shell Coupling of the $SO_3^-$-Groups 50 of the partially brominated gel (see above) was transferred to a flask and mixed with 5 g of sodium sulphite dissolved in 100 mL distilled water. While stirring, 50% NaOH is added to pH 12, followed by stirring for 16 h at 50° C. The gel was then washed with distilled water on a glass filter.

The amount of $SO_3^-$-groups attached was estimated to 50 µmol/mL.

Activation (Bromination) of the Core 50 mL of the shell coupled beads (see above) was weighed into a flask and 50 mL of distilled water and 2.0 g sodium acetate were added. A Bromine (saturated aqueous solution) was added until a persistent yellow colour was obtained, followed by destruction of excess bromine with sodium-formiate and washings with distilled water on a glass filter.

Dextran Coupling in the Core of the Beads 50 g of Dextran (MW: 150 000 g/mol) were dissolved in 50 mL of distilled water by slow stirring at ambient temperature for 2-4 h. 50 mL drained core activated HFA 55 beads ($SO_3^-$-groups attached in the shell) were added to the dextran solution, and the solution was stirred at 50° C. for 1 h. While stirring, 6.25 mL of 50% NaOH was added. The solution was stirred for 16 h at 50° C. and then washed on a glass filter with distilled water.

Experiment 1: Purification of Insulin from Cleaved Proinsulin on Reference Resin Capto SP ImpRes Insulin is purified from cleaved proinsulin. There are three contaminants that are to be removed, a prepeak, truncated insulin and a major contaminant. This has successfully been done by using reference resin Capto SP ImpRes (FIG. 2).

Figure 2:
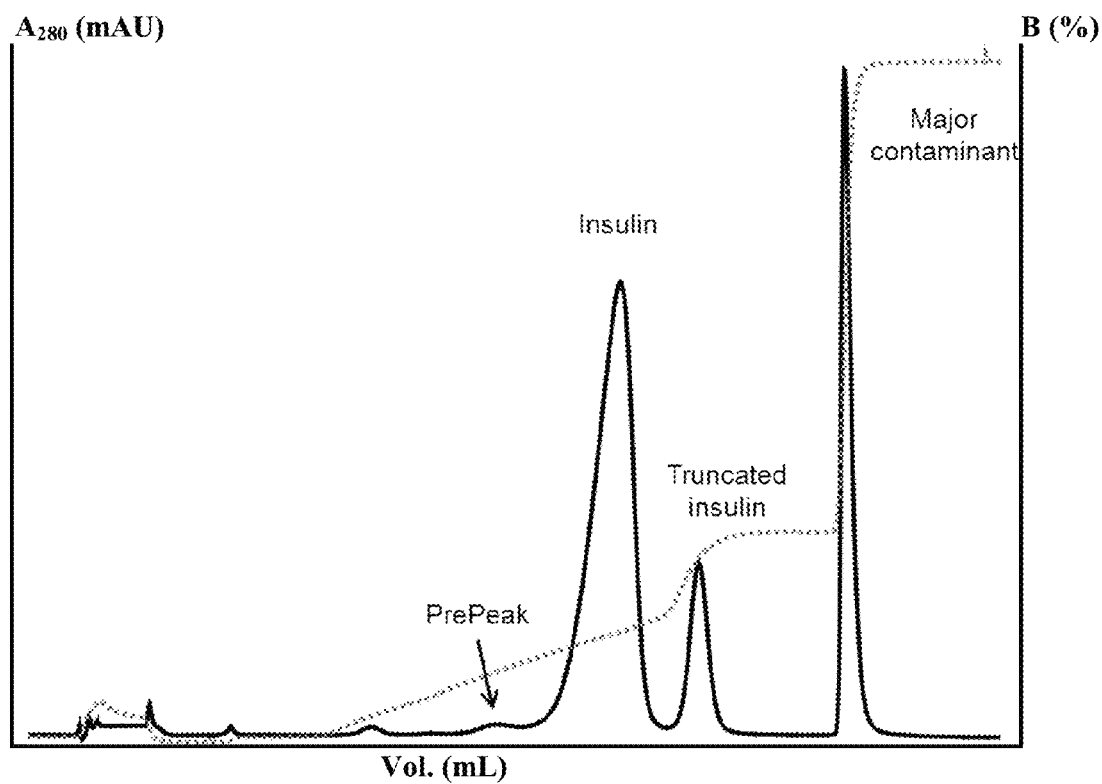
FIG. 2 Graph showing purification of insulin using shell bead chromatography.

FIG. 2 shows purification of insulin on a 1-ml Capto SP ImpRes (0.5 cm i.d.). The insulin feed concentration was 9 mg/ml resin, loading volume was 2 ml. Buffer A was 50 mM sodium acetate, pH 4+47.5% ethanol. Buffer B was 50 mM sodium acetate, pH 4, 250 mM NaCl+47.5% ethanol. Gradient was 0-60% buffer B in 10 column volumes. The major contaminant was eluted with buffer A containing 1 M NaCl. Flow rate was 0.4 ml/min (5 min residence time). The UV trace and the conductivity are shown.

Experiment 2: Comparison of the Purification of Insulin on Different Shell Bead Prototypes in Relation to Reference Resins The purification is done in the presence of high concentration of ethanol and the load is relatively low (~18 g/L) due to possible aggregation/fibrillation issues. The presence of ethanol gives relatively high back-pressure which is not desirable. Therefore the potential of using shell bead constructs on a larger bead (lower back-pressure) to avoid pressure-flow limitations has been investigated. Comparison of the back-pressure over Capto SP ImpRes and the larger shell bead is shown in FIG. 3.

Figure 3:
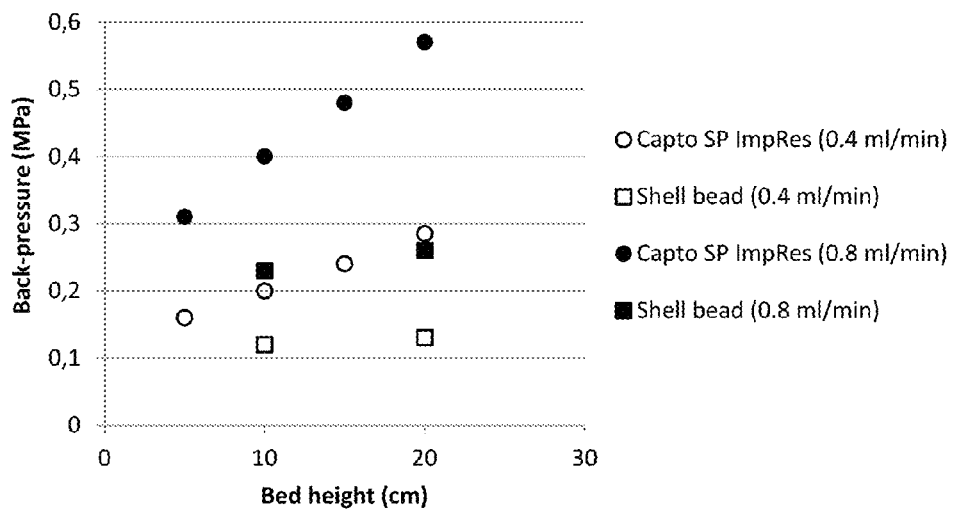
FIG. 3 Effect of bed height and flow rate on the backpressure over columns packed with two different media.

FIG. 3 shows the effect of bed height and flow rate on the back-pressure over columns packed with Capto SP ImpRes (40 µm) and Shell beads S6, S20 and S26 (77 µm). The flow rates 0.4 ml/min and 0.8 ml/min correspond to linear flow rates of 120 cm/h and 240 cm/h, respectively.

Figure 4:
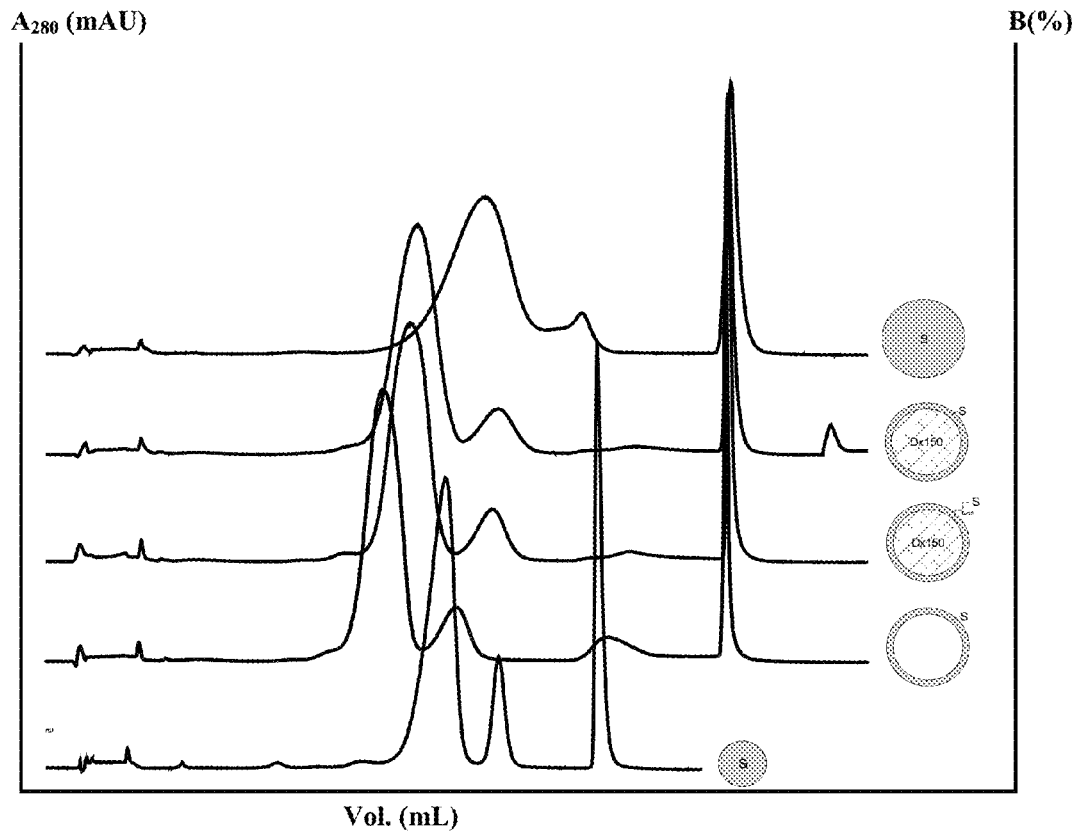
FIG. 4 Comparison of the purification of insulin using commercial media and shell bead media used in the invention.

The shell bead constructs were tested for their insulin purification potential. The results showed that it was possible to purify insulin to a purity of >90% (with prototype S20) with the shell beads (FIG. 4). As expected the resolution on the fully functionalized reference prototype, S12, was much worse than on the shell bead prototypes.

FIG. 4 shows comparison of the purification of insulin on a 1-ml Capto SP ImpRes (0.5 cm i.d.) and on 2-ml shell bead prototypes (0.5 cm i.d.). The insulin feed concentration was 9 mg/ml resin, loading volume was 2 ml (Capto SP ImpRes) or 4 ml (shell bead prototypes). Buffer A was 50 mM sodium acetate, pH 4+47.5% ethanol. Buffer B was 50 mM sodium acetate, pH 4, 250 mM NaCl+47.5% ethanol. Gradient was 0-60% buffer B in 10 column volumes. The major contaminant was eluted with buffer A containing 1 M NaCl. A residence time of 2.5 min (240 cm/h) for the shell bead prototypes, while it was 5 mM for Capto SP ImpRes.

Figure 5:
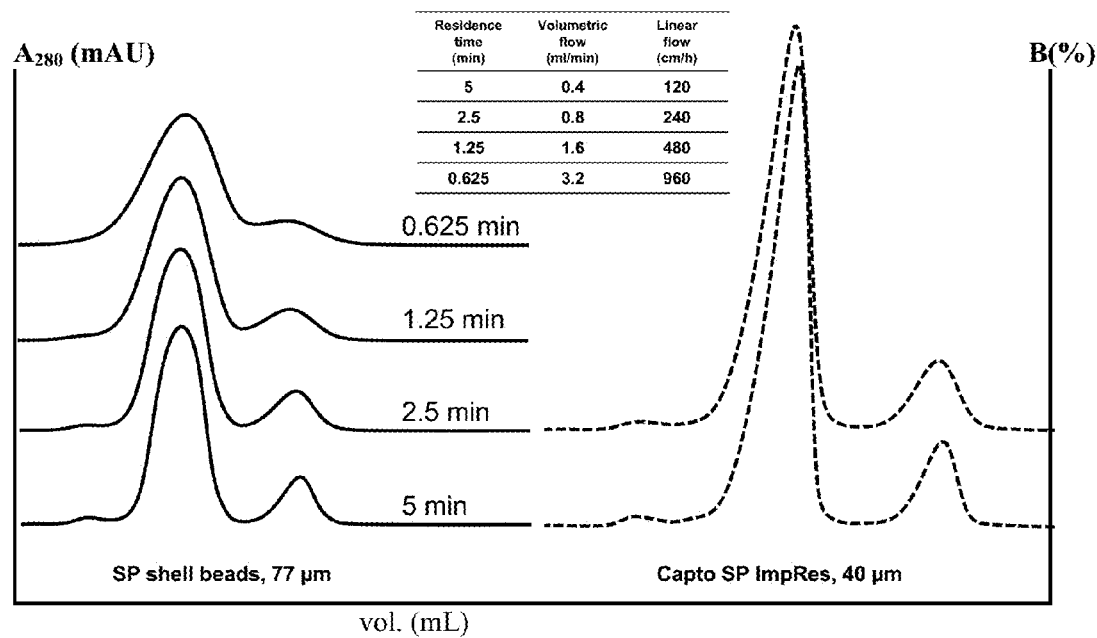
FIG. 5 Shows the effect of flow rate on commercial media and shell bead media used in to the invention.

Experiment 3: Effect of Flow Rate on the Separation of Insulin from Contaminants on Shell Bead Prototypes and Reference Resin The separation was good on reference resin Capto SP ImpRes at flow rates of 120 and 240 cm/h, respectively. However, for the shell beads separation was good at flow rates up to 480 cm/h (FIG. 5). The purity was >90% on the shell beads at flow rates up to 480 cm/h.

FIG. 5 shows the effect of flow rate was investigated on Capto SP ImpRes and a shell bead prototype (S20). The column volume was 2 ml for both resins. The insulin feed concentration was 9 mg/ml resin. Loading volume was 4 ml. Buffer A was 50 mM sodium acetate, pH 4+47.5% ethanol. Buffer B was 50 mM sodium acetate, pH 4, 250 mM NaCl+ 47.5% ethanol. Gradient was 0-90% buffer B in 15 column volumes.

Experiment 4: Insulin Purification on Reference Resin and on Shell Bead Prototypes Made with the Same Base Matrix as Reference Resin (Capto SP ImpRes)

It has been shown in the above experiments that good purification can be achieved on a large bead (77 μm) if the shell bead concept used.

In this experiment, the shell bead concept was applied to the smaller bead (40 μm) of Capto SP ImpRes. Two different shell thicknesses were functionalized, 2 and 5 μm, respectively. As expected, the shell bead prototypes had an improved resolution over Capto SP ImpRes (FIG. 6).

Figure 6:
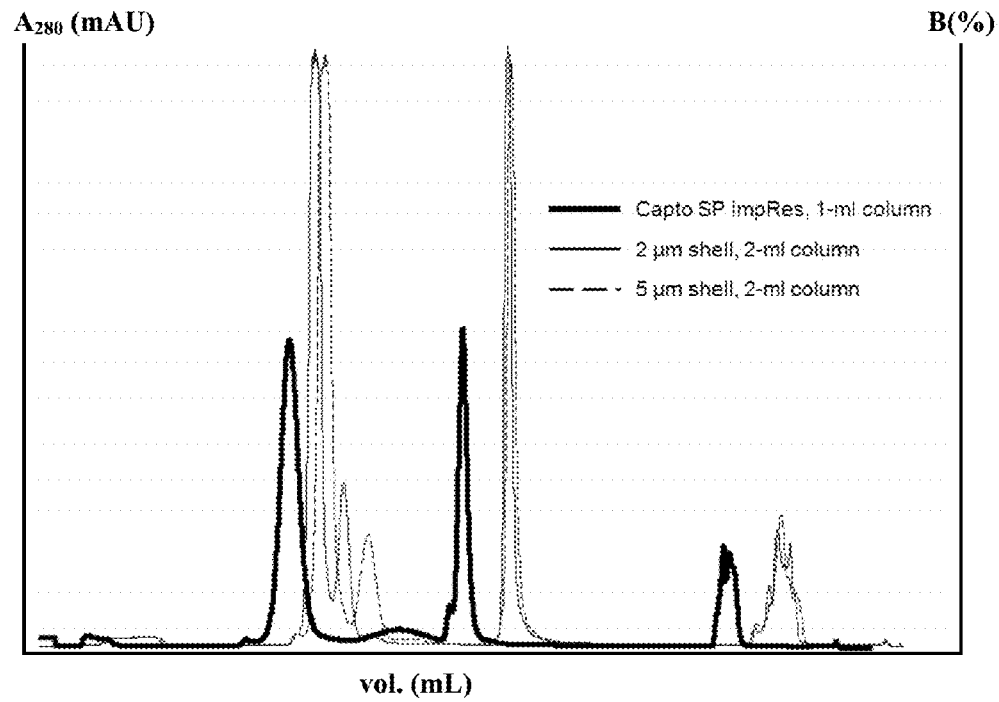
FIG. 6 Shows the results of insulin purification on commercial media and shell bead media.

FIG. 6 shows insulin purification on Capto SP ImpRes and on shell bead prototypes made with the same base matrix as Capto SP ImpRes. The shell bead prototypes had a functionalized layer of 2 μm and 5 μm, respectively. The load was 6.5 mg cleaved insulin/ml resin in 50 mM sodium acetate, pH 4 and 10% ethanol. Step elution 1 was done with 50 mM sodium acetate, pH 4, 170 mM NaCl, 50% ethanol. Step elution two was as step elution 1, except that the NaCl concentration was 1 M.

Results and Discussion

A comparison of estimated productivity obtained on a HFA SP Shell Bead prototype and Capto SP ImpRes has been performed, using realistic data from an insulin processes.

Productivity calculations were performed looking at the CIEX step only.

SuperPro Designer, version 8.5, Build 3, from Intelligen Inc. was used for all simulations. The simulation was made for processing insulin at a concentration of 15 g/L. The concentration, 15 g/L was chosen as an average concentration of insulin in this step. Yield was 85% for both resins. Bed height used for simulation: 20 cm.

The simulation was made by using a loading-step flow of 480 cm/h for the HFA SP Shell bead prototype and 120 cm/h for Capto SP ImpRes. This gives a residence time (RT) of 2.5 minutes for the HFA SP Shell bead prototype and 10 min for Capto SP ImpRes. All other flow rates was set to 600 cm/h for the HFA SP Shell bead prototype and 250 cm/h for Capto SP ImpRes, except for the regeneration/CIP step that for both resins was set at a defined time, i.e. 15 minutes. For both resins a working/effective capacity of 20 g insulin/L resin was used.

The simulated polishing step contained the following operations:
Equilibration: 4 CV for Capto SP ImpRes, 2 CV for HFA SP Shell beads
Load: 50 g insulin/L resin
Wash: 3 CV
Elution: 15 CV Gradient 0-70% 25 CV and 3 CV 100%
CIP: 15 min
Re-equilibration: 4 CV, for Capto SP ImpRes, 2 CV for HFA SP Shell beads The operating time for the process using the HFA SP Shell bead prototype is 1 hours and 8 minutes while the process including Capto SP ImpRes takes 2 hours and 39 minutes. Table 1 shows the result from these two simulations.

TABLE 1

Results obtained in the productivity simulation.

| Resin | Flow (cm/h) (loading) | Residence time (min) (loading) | Flow (cm/h) (other steps) | Time (h & min) | Productivity (kg/h) |
|---|---|---|---|---|---|
| HFA SP Shell Bead | 480 | 2.5 | 600 | 1:08 | 7.58 |
| Capto SP ImpRes | 120 | 10 | 250 | 2:39 | 3.22 |

Based on these set of simulations one can see that the productivity would be approximately double for the HFA SP Shell Bead prototype compared to Capto SP ImpRes.

The invention claimed is:

1. A method for purification of insulin from pro-insulin comprising the following steps:
   loading a sample of cleaved pro-insulin onto a chromatography medium comprising porous shell beads having an inner core and an outer layer, wherein the inner core is non-functionalized while the outer layer is functionalized with ion exchange ligands;
   adsorbing insulin on the ion exchange ligands; and
   eluting insulin from the chromatography medium at a flow rate of 100-1000 cm/h, wherein the eluted insulin has a purity of more than 85%.

2. The method of claim 1, wherein the porous shell beads are 20-100 μm in diameter.

3. The method of claim 1, wherein the porous shell beads are 40-80 μm in diameter.

4. The method of claim 1, wherein the functionalized layer of the porous shell beads comprises a 3-9 μm thick layer.

5. The method of claim 1, wherein the functionalized layer of the porous shell beads comprises a 5-7 μm thick layer.

6. The method of claim 1, wherein the ion exchange ligand is a strong cation exchange group selected from the group consisting of sulphonate ($SO_3^-$), sulphate ($—OSO_3^-$), phosphate ($—OPO_3^{2-}$), and phosphonate ($PO_3^{2-}$).

7. The method of claim 1, wherein the inner core is filled with a polar polymer selected from the group consisting of agarose, dextran, cellulose, starch, and pullulan.

8. The method of claim 1, wherein the pro-insulin is produced from bacteria.

9. The method of claim 1, wherein the eluted insulin has a purity of more than 90%.

10. The method of claim 1, wherein the flow rate is 300-600 cm/h.

11. The method of claim 1, wherein the inner core is inactive.

12. The method of claim 1, wherein the inner core is empty.

13. The method of claim 1, wherein the porous shell beads are 60-80 μm in diameter.

14. The method of claim 1, wherein the inner core is filled with a synthetic polymer selected from the group consisting of polyacrylic amide, polymethacrylic amide, and poly(hydroxyalkylacrylates).

* * * * *